United States Patent [19]

Fuller

[11] 4,164,517
[45] Aug. 14, 1979

[54] PREPARATION OF FLUORONITROBENZENE
[75] Inventor: George Fuller, Portishead, England
[73] Assignee: I.S.C. Chemicals Limited, London, United Kingdom
[21] Appl. No.: 866,007
[22] Filed: Dec. 30, 1977
[51] Int. Cl.$^2$ ............................................. C07C 79/12
[52] U.S. Cl. .................................................... 260/646
[58] Field of Search ......................................... 260/646
[56] References Cited
U.S. PATENT DOCUMENTS
4,069,262  1/1978  Kunz ..................................... 260/646

FOREIGN PATENT DOCUMENTS 2527944   8/1976  Fed. Rep. of Germany ........... 260/646
2724645  12/1977  Fed. Rep. of Germany ........... 260/646
1360327   7/1974  United Kingdom ..................... 260/646

Primary Examiner—Leland A. Sebastian
Attorney, Agent, or Firm—Holman & Stern

[57] ABSTRACT

A method of preparing a fluoronitrobenzene containing a fluorine atom in the para position with respect to the nitro group, comprising heating a polychloronitrobenzene or chloronitrobenzene containing a chlorine atom in the para position with respect to the nitro group with an alkali metal fluoride in the presence of sulpholane.

7 Claims, No Drawings

PREPARATION OF FLUORONITROBENZENE

This invention relates to the preparation of fluoronitrobenzenes, and more particularly to an improvement in or modification of the invention described and claimed in British Pat. No. 1,469,700.

British Pat. No. 1,469,700 describes and claims a method of preparing 2-fluoronitrobenzene wherein 2-chloronitrobenzene is heated with an alkali metal fluoride at a temperature of from 230° to 250° in the presence of sulpholane (tetrahydrothiophen-1:1-dioxide). The preferred molar ratio of sulpholane to organic starting material is from 0.3:1 to 0.9:1.

We have now discovered that the method of British Pat. No. 1,469,700 is equally applicable where a chlorine substituent is in the para position with respect to the nitro group and, in addition, even where other unaffected substituents, e.g. chlorine, are present in the meta position.

Thus the present invention consists in a modification of the invention claimed in British Pat. No. 1,469,700 wherein the starting material is a polychloronitrobenzene of fluorochloronitrobenzene containing a chlorine atom in the para position with respect to the nitro group.

In this specification, by "polychloronitrobenzene" there is meant an aromatic nitro compound having at least two chlorine atoms attached to ring carbon atoms.

Accordingly, the present invention provides a method of preparing a fluoronitrobenzene containing a fluorine atom in the para position with respect to the nitro group, comprising heating a polychloronitrobenzene or fluorochloro-nitro benzene containing a chlorine atom in the para position with respect to the nitro group with an alkali metal fluoride in the presence of sulpholane.

The polychloronitrobenzene starting material may have chlorine substituents at either or both of the ortho or meta positions with respect to the nitro group. However, where such a chlorine substituent is in the meta position it will not normally be liable to replacement by a fluorine atom, according to the method of the invention.

Where the starting material contains chlorine atoms in both the ortho and para positions with respect to the nitro group, the starting material is somewhat more reactive than if there is only one chlorine atom in either the ortho or para position and therefore the molar ratio of sulpholane to the organic starting material can be reduced somewhat. The preferred molar ratio in this case is from 0.1:1 to 3.0:1, i.e. moles sulpholane:moles dichloronitrobenzene, more preferably 0.1:1 to 0.9:1, still more preferably 0.1:1 to 0.5:1. The reaction temperature in this case is preferably from 180° to 250° C.

Generally at least one mole of alkali metal fluoride should be used per replaceable chlorine atom in the polychloronitrobenzene substrate.

Where the starting material is 3,4-dichloronitrobenzene the fluorination reaction gives, as the major product, 3-chloro-4-fluoro-nitrobenzene. The latter compound is readily converted into 3-chloro-4-fluoroaniline which is a valuable intermediate for the preparation of certain herbicides, e.g. isopropyl ($\pm$)-2-(N-benzoyl-3-chloro-4-fluoroanilino)-propionate which is sold under the trade-name "BARNON" (Registered Trade Mark).

Where the starting material is 2,4-dichloronitrobenzene the obtained difluoro-compound is a useful intermediate for the preparation of certain drugs. For example, the nitro compound may be reduced to give 2,4-difluoroaniline which is an intermediate for the preparation of the anti-inflammatory compound 2',4'-difluoro-4-hydroxy (1,1'-biphenyl)-3-carboxylic acid which is sold under the trade name "DIFLUNISAL."

The invention will be further described with reference to the following illustrative Examples.

Example 1 — Preparation of 3-chloro-4-fluoro-nitrobenzene.

A mixture of 3,4-dichloronitrobenzene (76.8g., 0.4 moles) and previously dried KF (25.5 g., 0.44 moles) in sulpholane (35 g.) was stirred at 240° for 24 hours in a 500 ml. 3-necked flask fitted with a polytetrafluoroethylene stirrer, a thermometer pocket and a reflux condenser. The cold reaction mixture was transferred to a rotating film evaporator flask, and the volatile part of the product was recovered under reduced pressure, noting the oil bath temperature during the distillation. Fraction 1 (41.02 g.) distilled at 30 mm. from an oil bath at 190°–200° C. and 3.2% of 3,4-dichloronitrobenzene, and 11% of sulpholane, whereas fraction 2(34.58 g.) distilled at 5 mm. from an oil bath at 180°–200° C. and contained a mixture of 41% of 3-chloro-4-fluoro-nitrobenzene, 6% of 3,4-dichloronitrobenzene and 52% of sulpholane.

The dichloronitrobenzene and sulpholane contents of the distilled fractions were calibrated, and the yields were calculated. 3-chloro-4-fluoro-nitrobenzene (48.3 g., 68.8% conversion) and 3,4-dichloronitrobenzene (3.3 g., 2.5% recovery) were obtained, and 22.7 g. of sulpholane (65% of input) were recovered.

EXAMPLE 2

The following Table 1 shows the reaction conditions for five runs carried out on the reaction of 2,4-dichloronitrobenzene(abbreviated to 2,4-DC1out on the reaction of 2,4-dichloronitrobenzene (abbreviated to 2,4-DC1NB) with previously dried potassium fluoride.

TABLE 1

| | KF and 2,4-DC1NB/Sulpholane (Reactant Quantities and Conditions) | | | | |
|---|---|---|---|---|---|
| Run No. | KF | 2,4-DClNB | Sulpholane | Temp(°C.)/time (hr.) | Mole Ratio Sulpholane 2,4-DC1NB |
| I | 38.3 g. (0.66 m) | 57.6 g. (0.3 m) | 30 g. (0.25 m) | 240°/6hr. | 0.83 |
| II | 66.1 g. (1.14 m) | 102.6 g. (0.53 m) | nil | 240°/30hr. | NIL |
| III | 65.8 g. (1.14 m) | 96.8 g. (0.5 m) | 16.1 g. (0.14 m) | 240°–218°/33hr. | 0.26 |
| IV | 65.0 g. (1.12 m) | 97.0 g. (0.5 m) | 16.2 g. (0.14 m) | 240°–236°/24hr. | 0.28 |

TABLE 1-continued

| | KF and 2,4-DClNB/Sulpholane (Reactant Quantities and Conditions) | | | | |
|---|---|---|---|---|---|
| Run No. | KF | 2,4-DClNB | Sulpholane | Temp(°C.)/time (hr.) | Mole Ratio Sulpholane 2,4-DClNB |
| V | 127.6 g. (2.2 m) | 192.0 g. (1.0 m) | 12.0 g. (0.1 m) | 238°–240°/24hr. | 0.10 |

In the above Table, M stands for moles.

In each case the reaction was carried out in a 250 ml. 3-necked flask fitted with a polytetrafluoroethylene bladed stirrer, a thermometer pocket and a single surface reflux condenser. During each reaction samples were withdrawn at intervals and the conversion of 2,4-dichloronitrobenzene into 2,4-difluoronitrobenzene was calculated from gas-liquid chromatography analysis of the sample according to the relationship:

$$\frac{\text{Conversion to}}{\text{2,4-DFNB}} = \frac{\text{2,4-DFNB} \times 100}{\text{2,4-DFNB} + \text{2Cl4FNB} + \text{2,4-DClNB}}$$

where
2,4-DFNB is 2,4-difluoronitrobenzene,
2Cl4FNB is a mixture of 2-chloro-4-fluoronitrobenzene and 4-chloro-2-fluoronitrobenzene,
2,4-DClNB is 2,4-dichloronitrobenzene In run II (no sulpholane used) there was a conversion of about 20% in 30 hours.

Where a mole ratio of sulpholane:2,4-dichloronitrobenzene of 0.1:1 was used (Run V) there was a conversion of 38.4% within 24 hours whereas with a mole ratio of 0.83:1 (Run I) a 94% conversion was achieved in only 6 hours. In Run III conversion was 63% in 24 hours. In Run IV conversion was 52% in 24 hours.

Thus the overall conclusion is that sulpholane increases the rate of the reaction and that it is preferably used in mole ratios ranging from 0.1:1 to 0.5:1 with respect to the dichloronitrobenzene.

The following Table 2 shows the reaction conditions and product analyses for a further six runs at different sulpholane:dichloronitrobenzene mole ratios and reaction conditions with the 2,4-dichloro-compound as starting material.

Table 2

| Run No. | KF | 2,4-DClNB | Sulpholane | Time (hr.) | Temp. (°C.) | Mole Ratio Sulpholane 2,4-DClNB | Product Analysis(%) | | | %KF utilized |
|---|---|---|---|---|---|---|---|---|---|---|
| | | | | | | | DFNB | ClFNB | DClNB | |
| VI | 220.5 g. (3.8 m) | 333.6 g. (1.74 m) | 68.7 g. (0.57 m) | 22 | 226–240 | 0.33 | 75.2 | 22.8 | 0.4 | 59 |
| VII | 351.3 g. (6.06 m) | 666.1 g. (3.47 m) | 237.7 g. (1.98 m) | 9 | 208–240 | 0.57 | 50.8 | 37.3 | 4.1 | 57.6 |
| VIII | 351.2 g. (6.06 m) | 666.1 g. (3.47 m) | 238.6 g. (1.99 m) | 9 | 230–240 | 0.57 | 67.8 | 29.3 | 0.7 | 68.0 |
| IX | 262.7 g. (4.53 m) | 498.1 g. (2.59 m) | 177.8 g. (1.48 m) | 13 | 229–240 | 0.57 | 57.3 | 37.0 | 1.8 | 75.7 |
| X | 40.0 g. (0.69 m) | 96.8 g. (0.50 m) | 34.6 g. (0.29 m) | 20 | 232–240 | 0.58 | 48.0 | 43.1 | 4.1 | 66.6 |
| XI | 283.8 g. (4.89 m) | 668.1 g. (3.48 m) | 242.2 g. (2.02 m) | 15.5 | 240–243 | 0.58 | 17.3 | 47.5 | 25.7 | 41.5 |

N.B. In the above Table, the "% KF utilized" represents the fluorine content of fluoronitrobenzenes in the product expressed as a percentage of fluorine present in the potassium fluoride input.

EXAMPLE 3

Fluorination of 2,4-dichloronitrobenzene with KF/Sulpholane at 200°

Four runs were carried out in which various charges of 2,4-dichloronitrobenzene, a mixture of 2-chloro-4-fluoronitrobenzene and 4-chloro-2-fluoronitrobenzene, and KF/Sulpholane are put into a reaction vessel which in every case was heated to 200° in about 4 hours (see Table 3). When the temperature had reached 200° the contents were sampled and analysed by gas-liquid chromatography, referred to as g.l.c., (see Table 4). The increase in difluoronitrobenzene content and the corresponding decrease in 2,4-dichloronitrobenzene content showed that significant fluorination had taken place at this stage.

Table 3

| | Input charge to KF/Sulpholane Reaction(Parts by wt.) | | | |
|---|---|---|---|---|
| Input | Run 1 | Run 2 | Run 3 | Run 4 |
| KF | 125 | 150 | 150 | 150 |
| Sulpholane | 254 | 425 | 290 | 265 |
| 2,4-DFNB | 6.2 (2.3%)* | — | 4.3 (1%)* | 8.7(2.3%) |
| 2Cl4FNB | 171.8(64.0%) | — | 119.6(26.8%) | 143.8(38.4%) |
| 2,4-DClNB | 90.5(33.7%) | 225(100%) | 323.0(72.3%) | 222(59.3%) |

*Percentage of total nitro-compound content

Table 4

| | g.l.c. analysis of product after heating to 200° during 4 hours | | | |
|---|---|---|---|---|
| Component | RUN 1 | RUN 2 | RUN 3 | RUN 4 |
| | * ** | | | |
| 2,4-DFNB | 7.48%(14.5%) | 7.64%(16.1%) | 7.53%(14.1%) | 31%(41.0%) |
| 2Cl4FNB | 30.87%(60.0%) | 16.93%(35.6%) | 15.57%(29.1%) | 28.2%(37.3%) |
| 2,4-DClNB | 13.09%(25.4%) | 22.92%(48.3%) | 30.36%(56.8%) | 16.5%(21.8%) |
| Sulpholane | 47.8% — | 52.2% — | 46.32% — | 22.9% — |

Key to Tables 3 and 4

2,4-DFNB is 2,4-difluoronitrobenzene

2C14FNB is a mixture of 2-chloro-4-fluoronitrobenzene and 4-chloro-2-fluoronitrobenzene 2,4-DC1NB is 2,4-dichloronitrobenzene Thus, Example 3 shows that significant fluorination occurs during heating the reaction mixture to 200° C. over 4 hours.

EXAMPLE 4

150 g (2.59 moles) of KF were suspended in 425 g (3.54 moles of sulpholane in a stirred flask. 225 g (1.17 moles) of 2,4-dichloronitrobenzene were added and the mixture heated to 230° C. and stirred at this temperature for 8 hours. The organic product after removal of sulpholane contained (by gas-layer chromatography)

75% by weight 2,4-difluoronitrobenzene;

22% by weight mixed chlorofluoro-nitrobenzenes and 1% by weight unchanged starting material.

Carbon recovery was about 65%.

I claim:

1. A method of preparing a fluoronitrobenzene containing a fluorine atom in the para position with respect to the nitro group, comprising heating a dichloronitrobenzene selected from the group consisting of (a) a dichloronitrobenzene containing chlorine atoms in the ortho and para positions with respect to the nitro group and (b) a dichloronitrobenzene containing chlorine atoms in the meta and para positions with respect to the nitro group, with potassium fluoride in the presence of a sulpholane at a temperature of about from 180° C. to 250° C., and wherein the mole ratio of sulpholane to said dichloronitrobenzene is from 0.1:1 to 3.0:1.

2. A method according to claim 1 in which chlorine atoms are present in the meta and para positions with respect to the nitro group in the dichloronitrobenzene.

3. A method according to claim 2 in which the sulpholane: dichloronitrobenzene mole ratio is from 0.3:1 to 0.9:1.

4. A method according to claim 2 in which the reaction temperature is from 230° to 250° C.

5. A method according to claim 1 in which chlorine atoms are present in the ortho and para positions with respect to the nitro group in the dichloronitrobenzene.

6. A method according to claim 5 in which the sulpholane:dichloronitrobenzene mole ratio is from 0.1:1 to 0.9:1.

7. A method according to claim 6 in which the sulpholane:dichloronitrobenzene mole ratio is from 0.1:1 to 0.5:1.

* * * * *